US010310107B1

(12) United States Patent
Yuan et al.

(10) Patent No.: US 10,310,107 B1
(45) Date of Patent: Jun. 4, 2019

(54) CALIBRATION AND MEASUREMENT METHOD AND SYSTEM FOR PIPING RADIOACTIVITY CONTAMINATION

(71) Applicant: INSTITUTE OF NUCLEAR ENERGY RESEARCH, ATOMIC ENERGY COUNCIL, EXECUTIVE YUAN, R.O.C., Taoyuan (TW)

(72) Inventors: Ming-Chen Yuan, Taoyuan (TW); Chin-Hsien Yeh, Taoyuan (TW)

(73) Assignee: INSTITUTE OF NUCLEAR ENERGY RESEARCH, ATOMIC ENERGY COUNCIL, EXECUTIVE YUAN, R.O.C. (TW)

( * ) Notice: Subject to any disclaimer, the term of this patent is extended or adjusted under 35 U.S.C. 154(b) by 0 days.

(21) Appl. No.: 16/121,709

(22) Filed: Sep. 5, 2018

(51) Int. Cl.
*G01T 1/167* (2006.01)
*G01T 7/00* (2006.01)

(52) U.S. Cl.
CPC .............. *G01T 7/005* (2013.01); *G01T 1/167* (2013.01)

(58) Field of Classification Search
CPC ................................. G01T 7/005; G01T 1/167
See application file for complete search history.

(56) References Cited

U.S. PATENT DOCUMENTS

| | | | | |
|---|---|---|---|---|
| 4,283,628 A | * | 8/1981 | Kulekov | G01N 23/18 378/60 |
| 5,656,817 A | * | 8/1997 | Bower | G01T 1/185 250/361 R |
| 5,665,972 A | * | 9/1997 | Dickinson | G01T 1/11 250/252.1 |
| 2014/0156067 A1 | * | 6/2014 | An | G01N 29/225 700/245 |

* cited by examiner

*Primary Examiner* — Marcus H Taningco
(74) *Attorney, Agent, or Firm* — Schmeiser, Olsen & Watts, LLP

(57) ABSTRACT

A calibration and measurement system for measuring a radioactive specific activity of an analyte pipe includes a calibration pipe, a standard radiation source, a radiation detector, a robot connected and a processing unit. The diameter of the inner wall of the calibration pipe is the same as the analyte pipe. The standard radiation source is surfaced over the inner wall of the calibration pipe and with a standard radioactive activity of a radioactive nuclide. The radiation detector is with a detection efficiency for detecting radiation. The radiation detector is for measuring the standard radioactive activity of the radioactive nuclide and a calibration net count rate thereof or measuring a radiation net count rate of the analyte pipe. The robot is connected with the radiation detector and moves in the calibration pipe or the analyte pipe. The processing unit calculates the detection efficiency and the radioactive specific activity.

10 Claims, 6 Drawing Sheets

US 10,310,107 B1

CALIBRATION AND MEASUREMENT METHOD AND SYSTEM FOR PIPING RADIOACTIVITY CONTAMINATION

FIELD OF THE INVENTION

The present disclosure relates to a calibration and measurement method and system, and in particular to a calibration and measurement method and system for measuring a radioactive specific activity of an analyte pipe by calibrating a detection efficiency of a radiation detector with a standard radiation source, and thereafter measuring the radioactive specific activity of the analyte pipe with a robot which carries the radiation detector moving into the analyte pipe.

BACKGROUND OF THE INVENTION

Numerous pipelines are widely distributed in ceilings, walls and floors of nuclear power plants, such as waste water drain pipes, water supply pump pipes, reactor drain pipes, safety injection pump drain pipes, drain ways of the valve housings, and the pumping rooms of the fuel pools.

Affected by radioactive materials, the inside of the pipeline is radioactively contaminated. When the radioactivity of the pipelines is contaminated to the extent that it needs to be decontaminated or scrapped, the pipelines will be removed. Hence, during the maintenance or the preparation for decommissioning of the nuclear power plant, the extent of radioactivity contamination of each pipelines will be measured.

The calibration and measurement for pipelines radioactivity contamination are multi-selective, e.g., smear sampling method, γ-spectrum analysis, scraping sampling with radiochemical analysis, and total acid etching method.

However, in the traditional measurement, the object sampled by the measurement is only part of the pipelines, so as the measurement result is not representative. Although γ-spectrum analysis is capable of measuring the radioactive activity of all parts of the pipeline from the outside of the pipeline, it is difficult to calibrate the measurement results due to the various shapes of the pipelines, so as the correct radioactivity cannot be measured.

SUMMARY OF THE INVENTION

According to one aspect of the present disclosure, a calibration and measurement method for piping radioactivity contamination measures a radioactive specific activity of an analyte pipe. The calibration and measurement method includes the following steps. Providing a calibration pipe, and the diameter of the inner wall of the calibration pipe is the same as the analyte pipe. Providing a standard radiation source which is with a standard radioactive activity of a radioactive nuclide. Surfacing the standard radiation source over the inner wall of the calibration pipe. Providing a radiation detector and a robot, and the robot is connected with the radiation detector. Placing the radiation detector and the robot into the calibration pipe. Operating the radiation detector to measure the standard radioactive activity of the radioactive nuclide and a calibration net count rate thereof. Calculating a detection efficiency of the radiation detector according to the ratio of the calibration net count rate to the standard radioactive activity. Placing the radiation detector and the robot into the analyte pipe. Operating the robot to drive the radiation detector moving in the analyte pipe. Operating the radiation detector to measure a radiation net count rate of the analyte pipe. Calculating the radioactive specific activity of the analyte pipe with the ratio of the radiation net count rate to the detection efficiency.

According to another aspect of the present disclosure, a calibration and measurement system for piping radioactivity contamination measures a radioactive specific activity of an analyte pipe. The calibration and measurement system includes a calibration pipe, a standard radiation source, a radiation detector, a robot connected and a processing unit. The diameter of the inner wall of the calibration pipe is the same as the analyte pipe. The standard radiation source is surfaced over the inner wall of the calibration pipe and with a standard radioactive activity of a radioactive nuclide. The radiation detector is with a detection efficiency for detecting radiation. The radiation detector is for measuring the standard radioactive activity of the radioactive nuclide and a calibration net count rate thereof, or for measuring a radiation net count rate of the analyte pipe. The robot is connected with the radiation detector and for moving in the calibration pipe or the analyte pipe. The processing unit is for calculating the detection efficiency according to the ratio of the calibration net count rate to the standard radioactive activity and for calculating the radioactive specific activity according to the ratio of the radiation net count rate to the detection efficiency.

DETAILED DESCRIPTION OF THE PREFERRED EMBODIMENTS

Implementation of the present disclosure is hereunder illustrated by specific embodiments. Persons skilled in the art can easily understand other advantages and effects of the present invention by referring to the disclosure contained in the specification.

Figure 1:
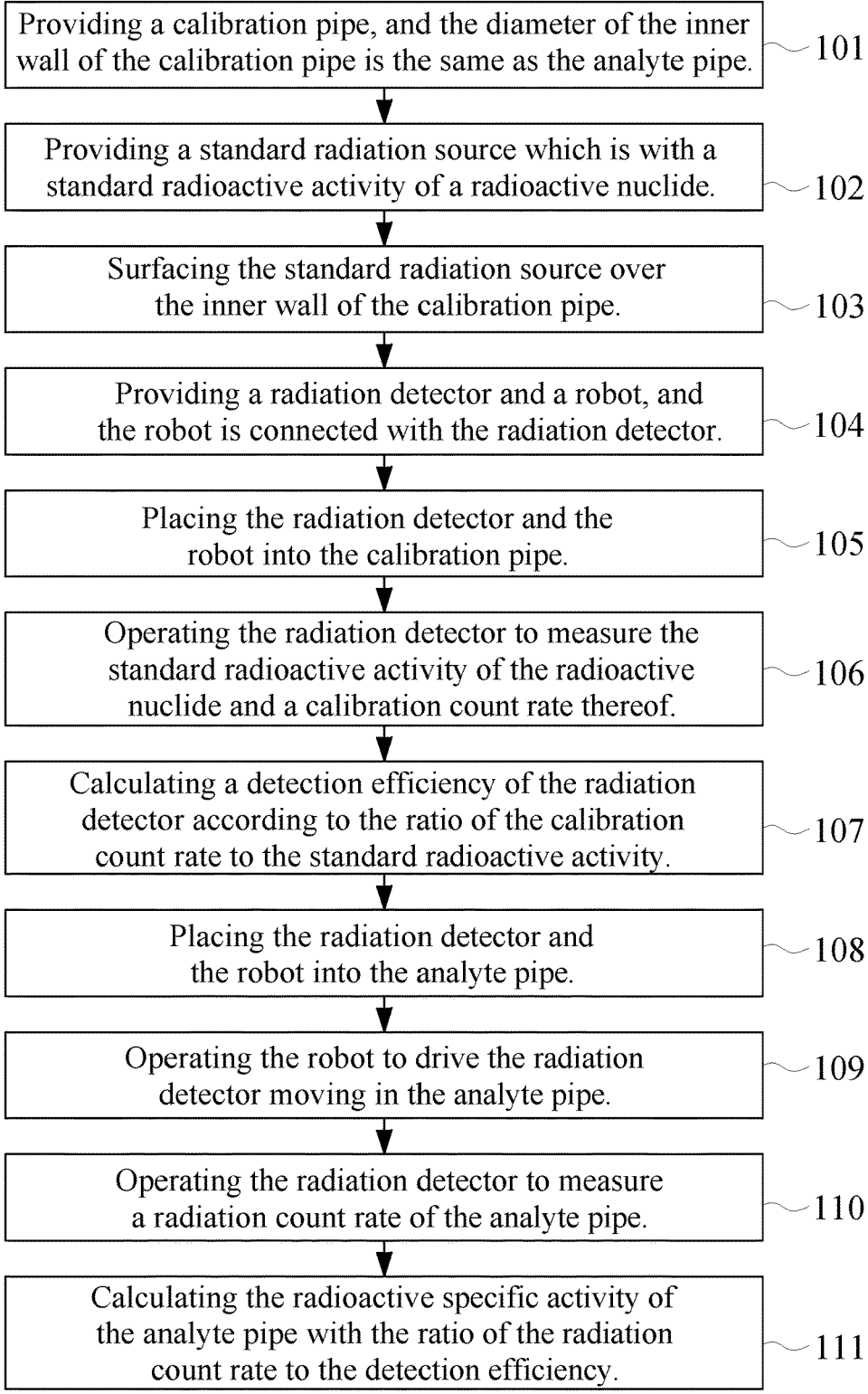
FIG. 1 is a flow chart of a calibration and measurement method for measuring a radioactive specific activity of an analyte pipe of the present disclosure.
Figure 2:
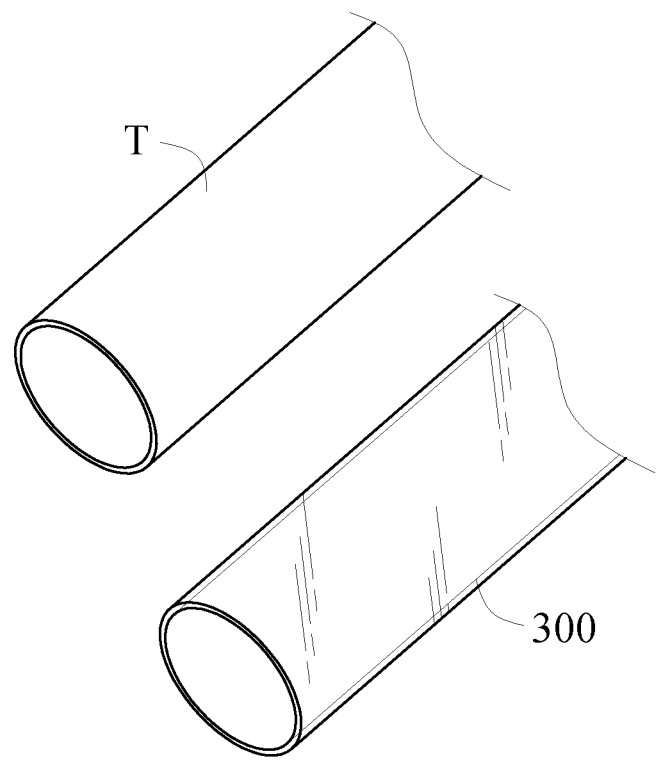
FIG. 2 is a schematic view of an analyte pipe and a calibration pipe of the present disclosure.
Figure 3:
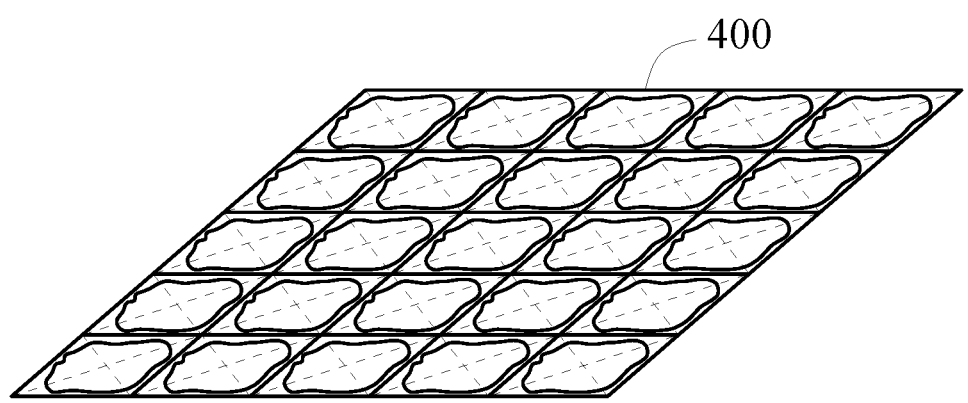
FIG. 3 is a schematic view of a standard radiation source of the present disclosure.

A calibration and measurement method 100 for piping radioactivity contamination measures a radioactive specific activity of an analyte pipe. Referring to FIG. 1 and FIG. 2, the calibration and measurement method 100 includes the following step. Step 101 is providing a calibration pipe 300, and the diameter of the inner wall of the calibration pipe 300 is the same as the analyte pipe T. Referring to FIG. 3, step 102 is providing a standard radiation source 400 which is with a standard radioactive activity of a radioactive nuclide, such as alpha, beta, and gamma. The size of the standard radiation source 400 is variable depending on the needs of the measurement. The standard radioactive activity of each standard radiation source 400 can be pre-measured with the instrument. The standard radioactive activity described herein is established by first measuring the radioactive activity in the calibration pipe 300 and then tracking the measurement results to the national radiation standard activity. The standard radiation source 400 can be Cobalt-60, Caesium-137, Europium-152 or Americium-241, but not limited thereto. The method of making a standard radiation source 400 and measuring the standard radiation activity is the background knowledge of those skilled in the art and will not be described in detail herein.

Figure 4A:
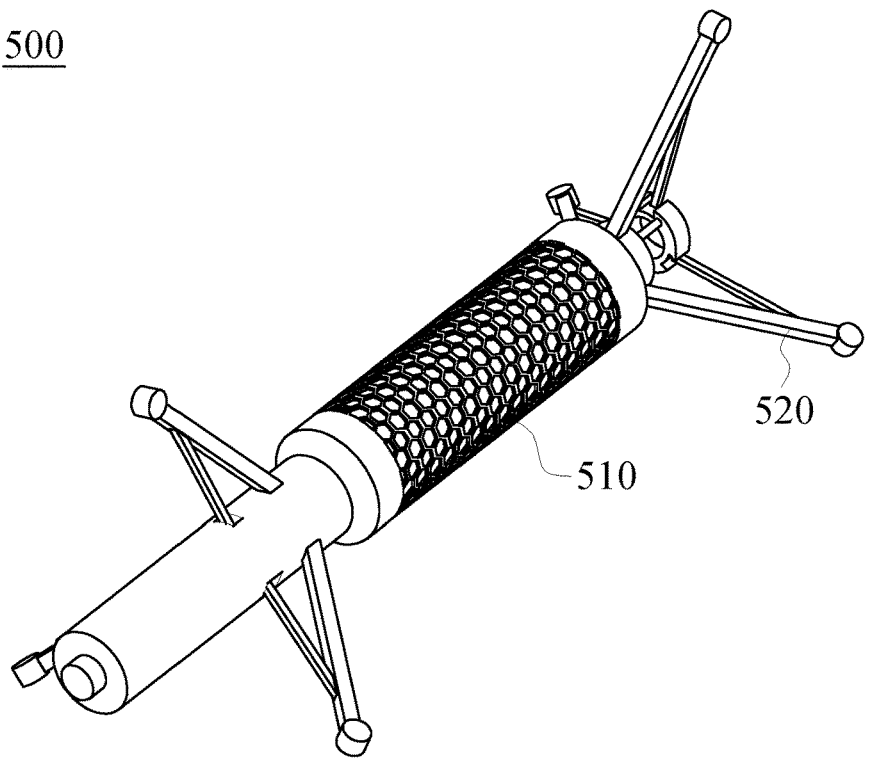
FIG. 4A is a schematic view of a columnar radiation detector of the present disclosure.

Referring to FIG. 4A to FIG. 6, step 103 is surfacing the standard radiation source 400 over the inner wall of the calibration pipe 300. In the embodiment, the standard radiation source 400 is a rollable sheet that automatically adapts to pipelines with different inside diameter. Step 104 is providing a radiation detector 500 and a robot 600, and the robot 600 is connected with the radiation detector 500. As shown in FIG. 4A and FIG. 4B, the surface of the radiation detector 500 is provided with one or more detection windows 510 for receiving and measuring the radiation of the environment inside the tube. The specifications of the radiation detector 500 can be changed according to the needs of the measurement. For example, the radiation detector 500 shown in FIG. 4A is columnar and provided a plurality of the detection windows 510 on the surface, so as to measure the radiation rapidly and extensively in long and straight pipelines. Furthermore, in FIG. 4B, the radiation detector 500 which is discoidal is advantageous for smoothly passing through the curved portion of the pipelines, and is therefore suitable for use in irregularly shaped pipelines. However, the radiation detector 500 shown in FIGS. 4A and 4B is only for explaining the present disclosure, and thus the embodiment of the radiation detector 500 is not considered to be a limitation. Step 105 is placing the radiation detector 500 and the robot 600 into the calibration pipe 300. Step 106 is operating the radiation detector 500 to measure the standard radioactive activity (Becquerel per cm²) of the radioactive nuclide and a calibration net count rate thereof. Step 107 is calculating a detection efficiency of the radiation detector 500 according to the ratio of the calibration net count rate (count per second, cps) to the standard radioactive activity.

In detail, since the geometry of the calibration pipe 300 is the same as the analyte pipe T, the calibration pipe 300 can simulate the environment within the analyte pipe T for measurement. Because the detection efficiency of the radiation detector 500 is the same in the same measurement condition (geometry), in step 106, the ratio of the calibration net count rate measured by the radiation detector 500 to the known standard radioactive activity (i.e., the detection efficiency) in the calibration pipe 300 will also be consistent with the analyte pipe T of the same condition. Accordingly, when the detection efficiency of the radiation detector 500 in the calibration pipe 300 has been determined, the radiation detector 500 can be applied to the same shape of the analyte pipe T.

In the embodiment, the detection efficiency is defined as below.

$$dectecttion\ efficiency\left(\frac{cps}{Bq/cm^2}\right) = \frac{calibration\ net\ count\ rate\ (cps)}{standard\ radioactive\ activity\ (Bq/cm^2)}$$

Figure 4B:
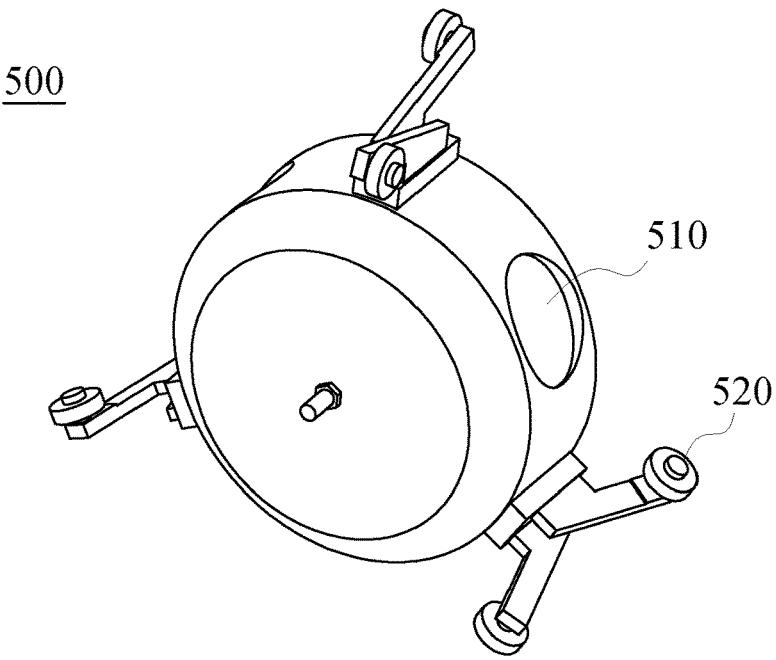
FIG. 4B is a schematic view of a discoidal radiation detector of the present disclosure.
Figure 5:
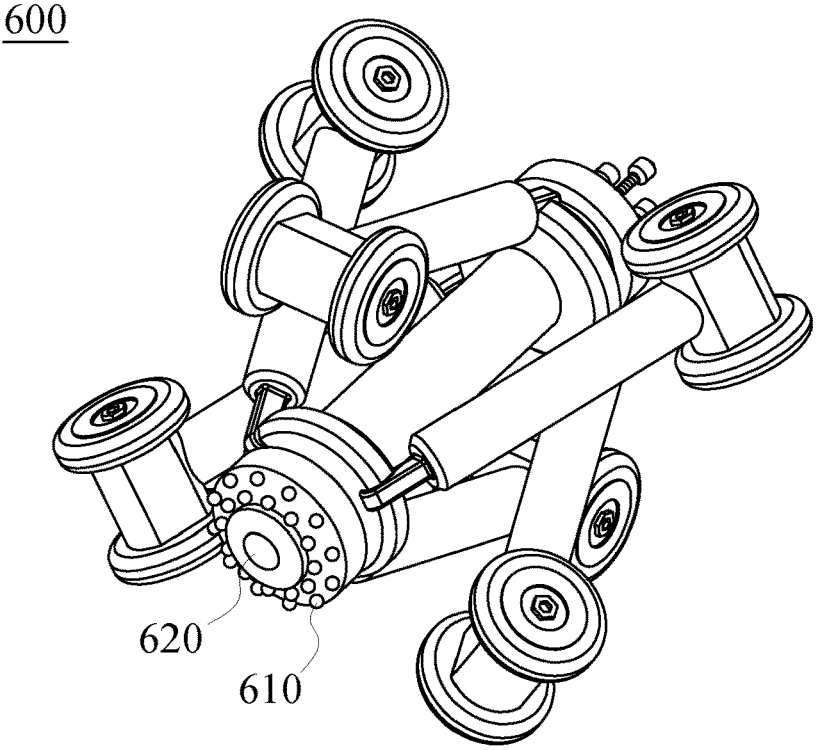
FIG. 5 is a schematic view of a robot of the present disclosure.
Figure 6:
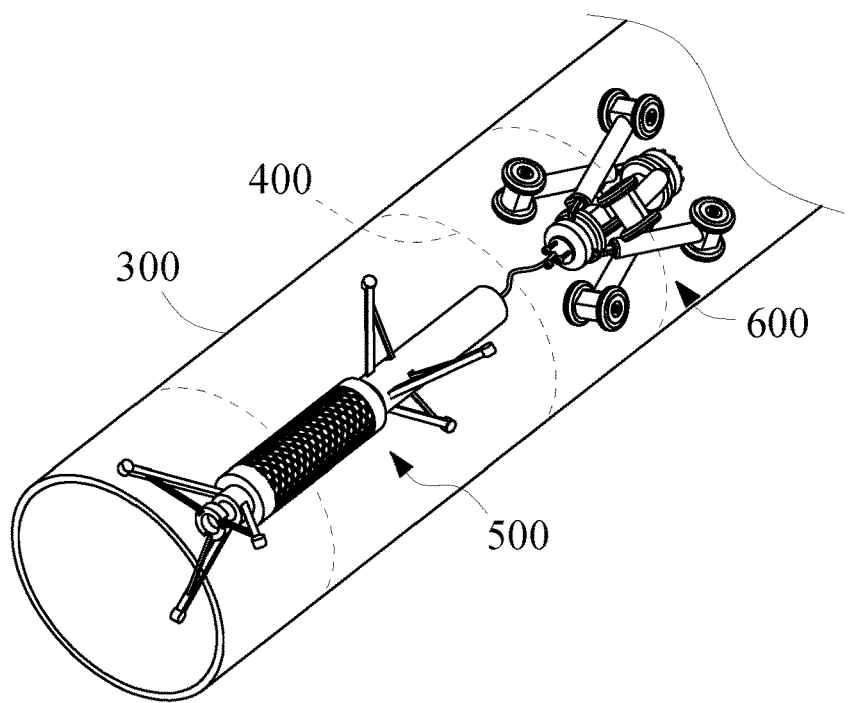
FIG. 6 is a schematic view showing the calibration of the detection efficiency of the calibration and measurement method of FIG. 1.

As shown in FIG. 4A and FIG. 4B, the radiation detector 500 measures the radioactivity of the pipelines with the detection windows 510 thereon. Therefore, the detection efficiency of each of the radiation detectors 500 may vary depending on the different specifications of the detection windows 510.

Figure 7:
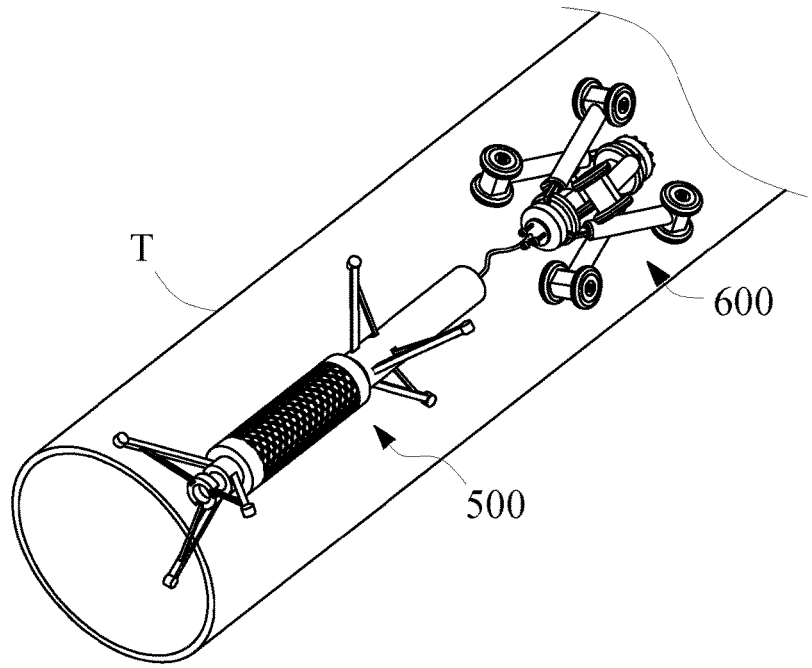
FIG. 7 is a schematic view showing measuring the radiation net count rate of the calibration and measurement method of FIG. 1.

Referring to FIG. 7, step 108 is placing the radiation detector 500 and the robot 600 into the analyte pipe T. Step 109 is operating the robot 600 to drive the radiation detector 500 moving in the analyte pipe T. Step 110 is operating the radiation detector 500 to measure a radiation net count rate of the analyte pipe T. Step 111 is calculating the radioactive specific activity of the analyte pipe T with the ratio of the radiation net count rate to the detection efficiency.

As described above, in a state where the detection efficiency of the radiation detector 500 is determined, the radiation net count rate of the analyte pipe T can be tested by the radiation detector 500.

It should be noted that the radiation net count rate is the result detected by the radiation detector 500, however, the result is affected by the detection efficiency of the radiation detector 500, hence the radiation net count rate is not equivalent to the actual radioactive specific activity.

The radioactive specific activity of the analyte pipe T is defined as below.

$$dectecttion\ efficiency\left(\frac{cps}{Bq/cm^2}\right) = \frac{calibration\ net\ count\ rate\ (cps)}{standard\ radioactive\ activity\ (Bq/cm^2)}$$

To summarize the above description, the calibration and measurement method 100 first pre-calibrates the detection efficiency of the radiation detector 500 by using a calibration pipe 300 which is the same geometry as the object to be tested. Thereafter, with the calibrated detection efficiency, the radiation net count rate is corrected, and so as to determine the actual radioactive specific activity.

The following table shows the measurement results of the columnar and discoidal radiation detector 500.

| radiation detector (columnar) | standard (Bq) | measurement (Bq) | difference (%) |
|---|---|---|---|
| Caesium-137 | 153972 | 184711 | 20 |
| Cobalt-60 | 160064 | 155670 | −3 |

| radiation detector (discoidal) | standard value (Bq) | measurement (Bq) | difference (%) |
|---|---|---|---|
| Caesium-137 | 153972 | 212889 | 38 |
| Cobalt-60 | 160064 | 214500 | 34 |

As shown in the above table, the present disclosure provides higher accuracy than the current measurement method. Moreover, because the radiation detector 500 is placed in the pipelines to measure the radiation, the measurement result is more representative and avoid the inaccuracies caused by local measurements.

Referring to FIG. 4A, FIG. 4B, FIG. 6, and FIG. 7, to ensure that the radiation detector 500 maintains stable movement in the analyte pipe T or the calibration pipe 300, the radiation detector 500 can be provided a plurality of casters 520 optionally. The position of the casters 520 can be adjusted to abut against the inner wall of the analyte pipe T or calibration pipe 300. In one embodiment, the radiation detector 500 is positioned by the casters 520 at the center of the section of the analyte pipe T or the calibration pipe 300, whereby the more accurate calibration net count rate and the radiation net count rate are measured.

In other embodiment, the calibration and measurement method 100 further provides a lighting unit 610 and a photographing unit 620. The lighting unit 610 and the photographing unit 620 are set on the front side of the robot 600, the lighting unit 610 is operable to illuminate the inner wall of the analyte pipe T, and the photographing unit 620 is used to capture one or more images of the inner wall of the analyte pipe T. With the further embodiment, the inner wall of the analyte pipe T can be observed while measuring the radioactive specific activity as a reference for other maintenance.

Figure 8:
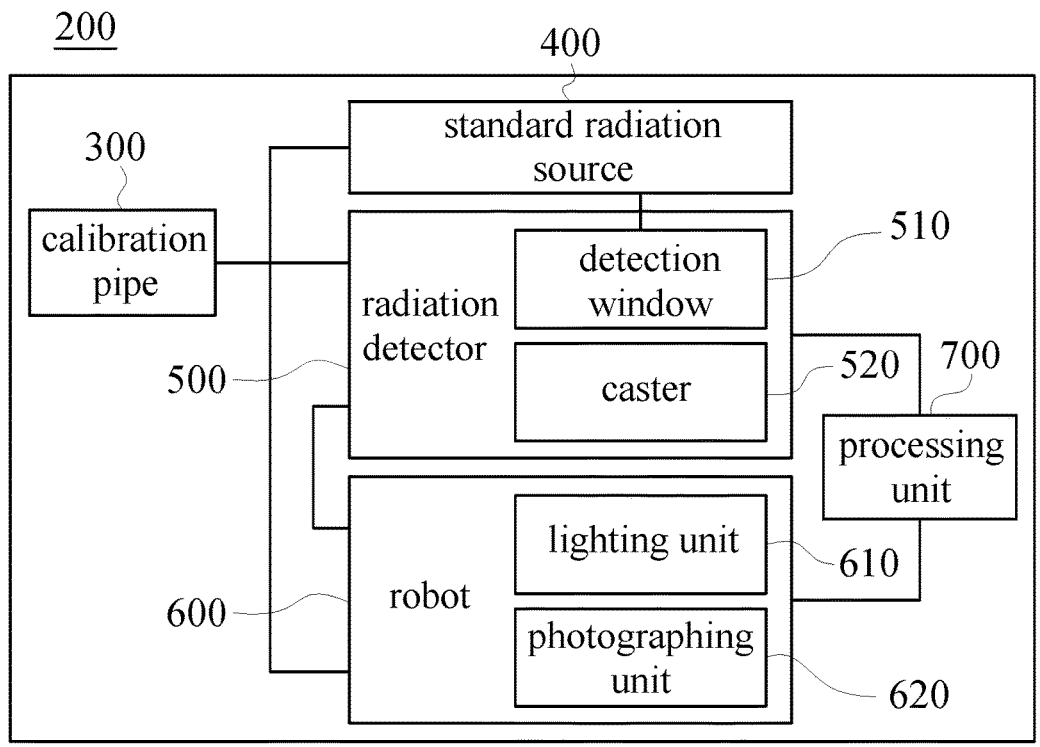
FIG. 8 is a block diagram of the calibration and measurement system of the present disclosure.

Referring to FIG. 1, FIG. 7, and FIG. 8, a calibration and measurement system 200 for piping radioactivity contamination measures a radioactive specific activity of an analyte pipe. The calibration and measurement system 200 includes a calibration pipe 300, a standard radiation source 400, a radiation detector 500, a robot 600, and a processing unit 700. The diameter of the inner wall of the calibration pipe 300 is the same as the analyte pipe T. The standard radiation source 400 is surfaced over the inner wall of the calibration pipe 300 and with a standard radioactive activity of a radioactive nuclide. The radiation detector 500 is with a detection efficiency for detecting radiation, the radiation detector 500 is for measuring the standard radioactive activity of the radioactive nuclide and a calibration net count rate thereof, or for measuring a radiation net count rate of the analyte pipe T. The robot 600 is connected with the radiation detector 500 and for moving in the calibration pipe 300 or the analyte pipe T. The processing unit 700 is for calculating the detection efficiency according to the ratio of the calibration net count rate to the standard radioactive activity; and for calculating the radioactive specific activity according to the ratio of the radiation net count rate to the detection efficiency.

The details of calibrating the detection efficiency and determining the count rate are as described in the aforementioned embodiment of the calibration and measurement method 100, and therefore will not be repeated herein.

In addition to receiving measurement data from the radiation detector 500 and calculating the radioactive specific activity, the processing unit 700 can also function as a controller for the calibration and measurement system 200. For example, the processing unit 700 is operable to control the robot 600 to move, turn on the lighting unit 610 and the photographing unit 620, or adjust the position of the caster 520 in a wired or wireless network to accommodate the variation in the inner diameter of the pipelines.

It is worth mentioning that under the condition that the geometry of the analyte pipe T is known, the detection efficiency of the radiation detector 500 can be pre-calibrated for on-site measurements. Consequently, the embodiment achieves a highly mobile radioactive contamination measurement operation, and can immediately determine the result of the contamination reaction.

In one embodiment, the standard radiation source 400 can be Cobalt-60, Caesium-137, Europium-152 or Americium-241, but not limited thereto. Moreover, the calibration and measurement system 200 can also provided with a lighting unit 610 and a photographing unit 620. The lighting unit 610 is disposed on the front side of the robot 600 for illustrating the inner wall of the analyte pipe T. The photographing unit 620 is disposed on the front side of the robot 600 for capturing one or more images of the inner wall of the analyte pipe T. The radiation detector 500 can be columnar or discoidal, but not limited thereto. The calibration and measurement system 200 can further provided with a plurality of casters 520. The casters 520 are disposed on the radiation detector 500. Each of the casters 520 abut against the inner wall of the analyte pipe T or the calibration pipe 300, so that the radiation detector 500 is positioned at the center of the section of the analyte pipe T or the calibration pipe 300.

The details and functions of the further embodiments are as described in the aforementioned calibration and measurement method 100, and therefore not described herein.

Figure 9:
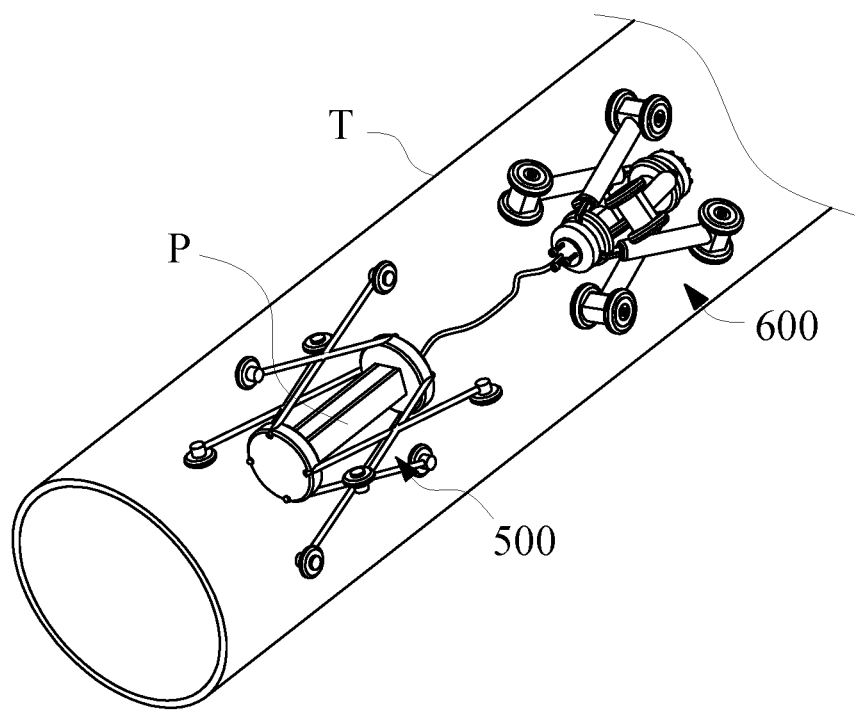
FIG. 9 is a schematic view showing the radiation detector carrying a cesium iodide crystal structure of the present disclosure.

In addition, in the embodiment of the calibration and measurement method 100 and the calibration and measurement system 200, the radiation detector 500 can also be utilized to test the nuclide of the radioactivity contamination within the pipeline. Referring to FIG. 9, the radiation detector 500 can carry a cesium iodide crystal structure P into the pipeline. The cesium iodide crystal structure is capable of detecting the gamma spectrum inside the pipeline, so as to identify the radioactive contamination of key nuclide such as cesium-137 or cobalt-60.

While the invention has been described by means of specific embodiments, numerous modifications and variations could be made thereto by those skilled in the art without departing from the scope and spirit of the invention set forth in the claims.

What is claimed is:

1. A calibration and measurement method for piping radioactivity contamination, the calibration and measurement method measuring a radioactive specific activity of an analyte pipe, comprising:
    providing a calibration pipe, the diameter of the inner wall of the calibration pipe being the same as the analyte pipe;
    providing a standard radiation source being with a standard radioactive activity of a radioactive nuclide;
    surfacing the standard radiation source over the inner wall of the calibration pipe;
    providing a radiation detector and a robot, the robot connected with the radiation detector;
    placing the radiation detector and the robot into the calibration pipe;
    operating the radiation detector to measure the standard radioactive activity of the radioactive nuclide and a calibration net count rate thereof;
    calculating a detection efficiency of the radiation detector according to the ratio of the calibration net count rate to the standard radioactive activity;
    placing the radiation detector and the robot into the analyte pipe;
    operating the robot to drive the radiation detector moving in the analyte pipe;
    operating the radiation detector to measure a radiation net count rate of the analyte pipe; and
    calculating the radioactive specific activity of the analyte pipe with the ratio of the radiation net count rate to the detection efficiency.

2. The calibration and measurement method of claim 1, wherein the standard radiation source is Cobalt-60, Caesium-137, Europium-152 or Americium-241.

3. The calibration and measurement method of claim 1, further comprising:
    providing a lighting unit and a photographing unit;
    setting the lighting unit and the photographing unit on the front side of the robot;
    operating the lighting unit to illustrate the inner wall of the analyte pipe; and
    operating the photographing unit to capture an image of the inner wall of the analyte pipe.

4. The calibration and measurement method of claim 1, wherein the radiation detector is columnar or discoidal.

5. The calibration and measurement method of claim 1, further comprising:
   providing a plurality of casters and setting the casters on the radiation detector; and
   adjusting the position of the casters to make each of the casters abut against the inner wall of the analyte pipe or the calibration pipe, and to make the radiation detector be positioned at the center of the section of the analyte pipe or the calibration pipe.

6. A calibration and measurement system for piping radioactivity contamination, the calibration and measurement system measuring a radioactive specific activity of an analyte pipe, comprising:
   a calibration pipe, the diameter of the inner wall of the calibration pipe being the same as the analyte pipe;
   a standard radiation source surfaced over the inner wall of the calibration pipe, the standard radiation source being with a standard radioactive activity of a radioactive nuclide;
   a radiation detector with a detection efficiency for detecting radiation, the radiation detector for measuring the standard radioactive activity of the radioactive nuclide and a calibration net count rate thereof, or for measuring a radiation net count rate of the analyte pipe;
   a robot connected with the radiation detector and for moving in the calibration pipe or the analyte pipe; and
   a processing unit for calculating the detection efficiency according to the ratio of the calibration net count rate to the standard radioactive activity; and the processing unit for calculating the radioactive specific activity according to the ratio of the radiation net count rate to the detection efficiency.

7. The calibration and measurement system of claim 6, wherein standard radiation source is Cobalt-60, Caesium-137, Europium-152 or Americium-241.

8. The calibration and measurement system of claim 6, further comprising:
   a lighting unit disposed on the front side of the robot for illustrating the inner wall of the analyte pipe; and
   a photographing unit disposed on the front side of the robot for capturing an image of the inner wall of the analyte pipe.

9. The calibration and measurement system of claim 6, wherein the radiation detector is columnar or discoidal.

10. The calibration and measurement system of claim 6, further comprising:
   a plurality of casters disposed on the radiation detector, each of the casters abut against the inner wall of the analyte pipe or the calibration pipe, so as the radiation detector being positioned at the center of the section of the analyte pipe or the calibration pipe.

* * * * *